United States Patent [19]
Bontemps

[11] Patent Number: 4,886,168
[45] Date of Patent: Dec. 12, 1989

[54] DEVICE DESIGNED TO PRESERVE COSMETIC SUBSTANCES THAT CAN BE FROZEN

[76] Inventor: Raymond Bontemps, 5 Avenue de la Grande Armée, 75008 Paris, France

[21] Appl. No.: 248,977

[22] Filed: Sep. 26, 1988

[30] Foreign Application Priority Data

Sep. 30, 1988 [FR] France ................ 87 13504

[51] Int. Cl.⁴ ............................ B65D 69/00
[52] U.S. Cl. ................ 206/568; 206/581; 206/229; 206/823; 132/317; 514/53; 514/54
[58] Field of Search ........... 206/223, 229, 568, 581, 206/524, 823; 132/293, 317, 318; 514/14, 53, 54

[56] References Cited

U.S. PATENT DOCUMENTS

| | | | |
|---|---|---|---|
| 1,935,639 | 11/1933 | Keeshaw | 132/317 |
| 3,214,012 | 10/1965 | Mack | 132/317 |
| 3,332,429 | 7/1967 | Bates | 132/317 |
| 4,294,349 | 10/1981 | Isben et al. | 206/568 |
| 4,735,935 | 4/1988 | McAnalley | 514/53 |
| 4,795,740 | 1/1985 | Cohen et al. | 514/14 |

FOREIGN PATENT DOCUMENTS 922611 12/1971 Canada .................... 206/568

*Primary Examiner*—David T. Fidei
*Attorney, Agent, or Firm*—Kramer, Brufsky & Cifelli

[57] ABSTRACT

The present invention concerns a container containing dehydrated cosmetic substances placed in a case and ampoules of physiological serum or some other solution. These substances, stored at ambient temperature, are impregnated with serum before being brought to freezing temperature prior to use. According to FIG. 1 the device is characterized by an isothermic plastic case (1) containing the substance and two ampoules (2) of serum placed separately in a container.

10 Claims, 2 Drawing Sheets

DEVICE DESIGNED TO PRESERVE COSMETIC SUBSTANCES THAT CAN BE FROZEN

FIELD OF THE INVENTION

The present invention concerns a container having a cylindrical or truncated-cone shaped plastic case sealed with a water-tight case, containing a cosmetic substance dehydrated by lyophilization. Two ampoules of serum or other solution are connected to this case and placed in the container. The cosmetological substance and the physiological serum are mixed at ambient temperature, then frozen at −30½ C. before being applied to the skin in order to obtain a cryogenic treatment of the skin.

BACKGROUND OF THE INVENTION

Currently, a number of fresh cosmetics of living origin are employed, free of all vehicles or preservatives, formed from a fetal substance, such as WHARTON jelly, mesenchyme, Meekel cartilage, the thymus, the amnion, utilized pure or in [various] combinations. These products are generally taken from an animal fetus, ground and reduced to a homogeneous paste. The latter is then dissolved in a physiological serum and packaged in the form of a solid bar at −80½ C.

These products are often of fetal origin, composed of biogens or specific cells based on DNA or RNA, which regenerates the living material. In addition, they are utilized in dermatology in the frozen state, by application onto the skin, in order to regenerate it rapidly. For example, massage of facial skin, which is effected by means of a frozen block composed essentially of substances of fetal origin or cosmetological substances, induces a localized melting of these substances. Due to the cold, the skin undergoes vasoconstriction, bringing about the release of dead particles or oils contained in the pores, while the warming which follows promotes the absorption of the fetal or cosmetological substances present on the skin, which penetrate and regenerate it.

Until now, after each use, the block was replaced in a container at −80½ C.

Moreover, this application technique necessitates the utilization of rods covered with a substantial volume of the frozen fetal substance designed to create a freezing inertia.

To facilitate the manipulation of these rods and limit the amount of warming they undergo by being handled, the latter are provided with a handle of plastic or non-heat-conducting wood. The protection of these rods is assured by a plastic case which can be adapted onto a washer of the appropriate dimensions, integral with the handle, in order to obtain a good seal.

These devices present a number of disadvantages, notably:

the fetal substance must always be stored in a container at −80½ C. between applications,
a large amount of living substances is used,
a major loss of fetal substances occurs,
it has an high cost of utilization [and],
manipulation is difficult.

SUMMARY OF THE INVENTION

The present invention alleviates these disadvantages by presenting a container that keeps the fetal substance or cosmetic dehydrated, so that it can be stored at ambient temperature.

The device is designed to preserve freezable cosmetic substances of fetal origin and characterized in that it is made up of a container having an isothermic plastic case sealing the dehydrated substance, two ampoules of isolated physiological serum, a filling assembly for the case, and a means of isolated handling.

The invention is thus characterized by a number of advantages, notably:

Simplified storage, which can be realized at ordinary temperatures,
Flexible manipulation,
Good preservation of the fetal substances,
An economy of active material.

BRIEF DESCRIPTION OF THE DRAWING

The invention will be better understood with the aid of the attached drawings, which show one preferred mode of embodiment, notably as concerns shape, volume, and the nature of materials used.

DETAILED DESCRIPTION

Figure 1:
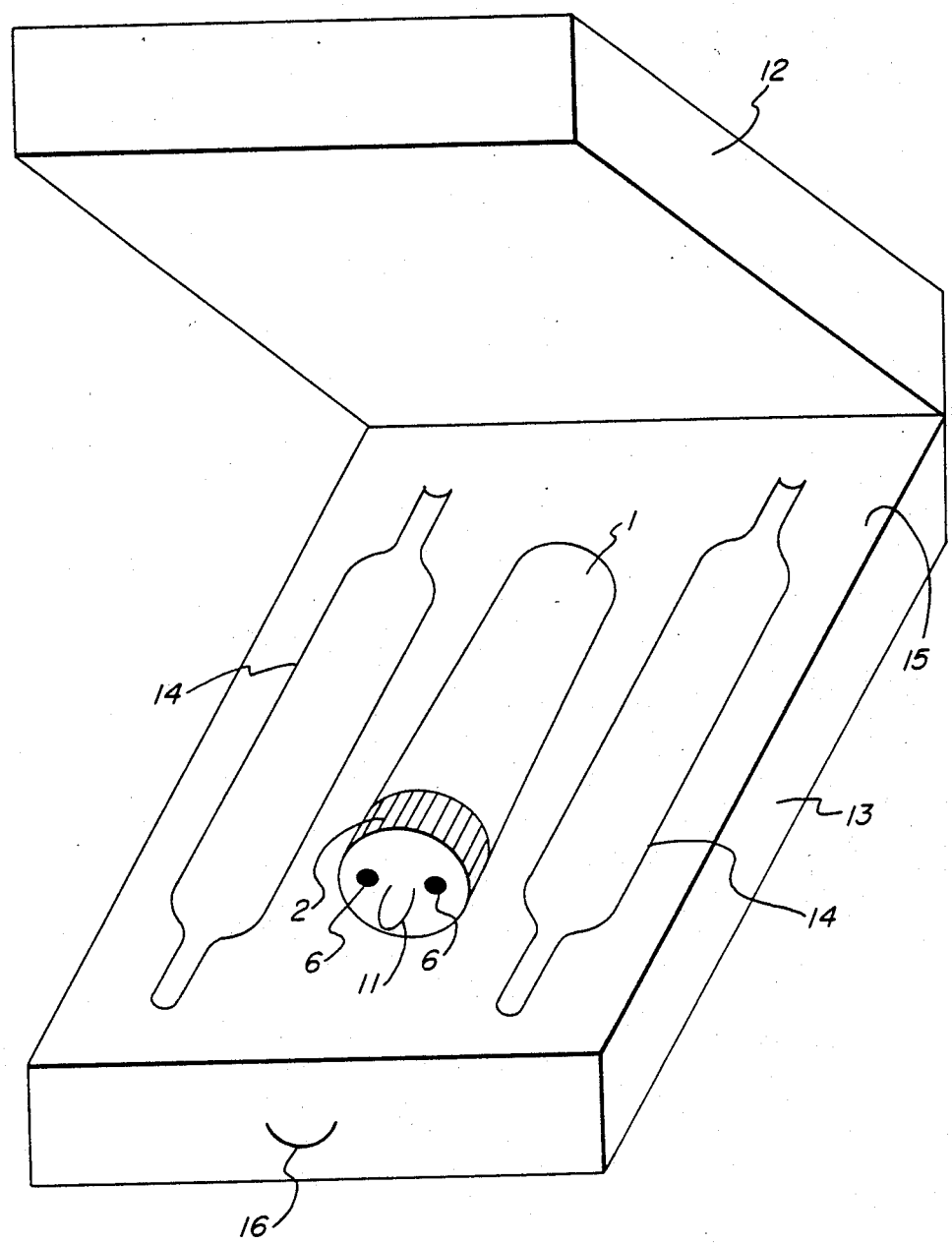
FIG. 1 shows the open container where the case and the ampoules of physiological serum are lodged.

According to an important characteristic of this invention, FIG. 1 shows that the container (13) is sealed by a case (12). Inside this container, the plastic case containing the dehydrated fetal or cosmetic substance is found. This case is sealed at the base by a plastic cover piece (2) which fits perfectly onto the case. There are orifices (6) on this cover piece, utilized for filling the case with physiological serum. The isothermic gripping rod (11) allows manipulation of the rod.

Two ampoules of physiological serum (14) are attached on both sides of the case (1). The assembly of the case and the ampoules of serum are lodged in a bed of expanded foam (15) in order to prevent shocks during transportation. When the container is closed, it can also be easily manipulated by the hand grip (16).

Figure 2:
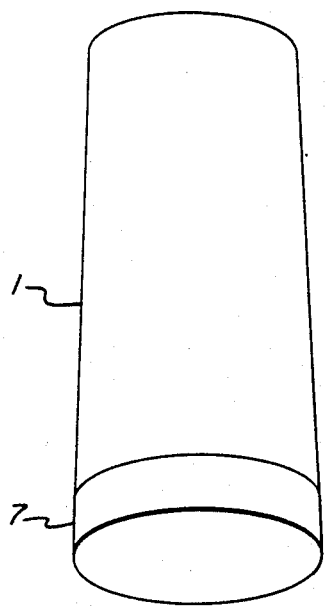
FIGS. 2 and 3 show the case and the plug holding the frozen substance.
Figure 3:
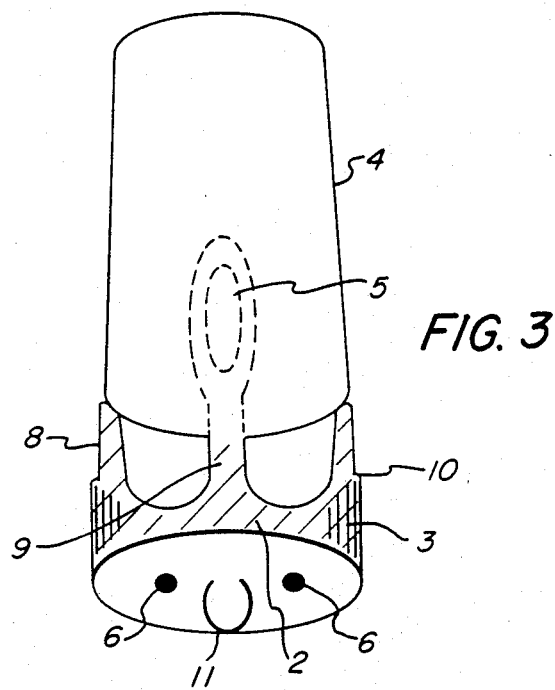

FIGS. 2 and 3 show the case and the cover piece supporting the fetal or cosmetic substance.

The plastic case, in truncated-cone form, has a base (7) of cylindrical section, which fits perfectly into the cover piece at level (8).

The cover piece represented by FIG. 3 is made up of a pedestal (2) supporting a ring (8) serving to house the case. The shoulder (10) assures a tight seal between the case (1) and the cover piece (3). A tongue (5), which starts at the end of the cover piece emerges and supports the fetal substance (4) when the former, soaked with physiological serum, is frozen.

The orifices (6) are used to fill the case with serum or solution. The tongue (11) permits handling of the assembly.

The grooves of the ring (2) facilitate the disconnection between the case and cover piece.

The elements 2, 5, 8 are made of molded plastic and formed into a single block.

The case, filled beforehand with fetal substance dehydrated by lyophilization, is transported at ordinary temperatures. When one wishes to effect a cosmetologic application, the case containing the substance is filled with serum by introducing the latter by way of one of the orifices (6) and placing it in a freezer at −30½ C. After freezing, the case is separated from the pedestal (3) and one can carry out the treatment by application to the skin.

What is claimed is:

1. A device for storing a freezable substance of fetal or cosmetic origin at ambient temperature, comprising:
   an isothermic case for containing a dehydrated fetal or cosmetic substance, said case having a generally cylindrical wall, a closed end and an open end;
   a cover for closing and reopening the case, said cover including a base portion and an annular portion extending from the base portion, said annular portion sized and shaped to fit in a sealing engagement with a portion of the generally cylindrical wall defining the open end of said case; and
   means for communicating a rehydrating substance from an external source to within the closed case.

2. A device according to claim 1, wherein the means for communicating comprises at least one orifice disposed in the base portion of the cover; said at least one orifice adapted for receiving a rehydrating substance from the external source.

3. A device according to claim 1, further comprising a member projecting from an inside surface of the base portion of the cover to within the closed case for supporting the fetal or cosmetic substance when it is rehydrated and frozen.

4. A device according to claim 1, wherein the cover is formed of an isothermic plastic.

5. A device according to claim 1, wherein the external source comprises at least one ampoule and the rehydrating substance is a physiological serum.

6. A device according to claim 1, wherein
   an end portion of the case, adjacent to the open end thereof is cylindrical;
   a remaining portion of the wall of the case forms a truncated cone; and
   the closed end of the case is disposed at the smaller end of the truncated conical wall.

7. A device according to claim 3, wherein the member has a first end integral with the base and a second end projecting within the closed case; and a hole is formed in the second end of the member.

8. A method for preparing a freezable substance of fetal or cosmetic origin for cosmetological application, comprising the steps of:

(A). containing a dehydrated or cosmetic fetal substance in a closed device, at ambient temperature, said device comprising:
   an isothermic case for containing a dehydrated fetal or cosmetic substance, said case having a generally cylindrical wall, a closed end and an open end;
   a cover for closing and reopening the case, said cover including a base portion and an annular portion extending from the base portion, said annular portion sized and shaped to fit in a sealing engagement with a portion of the generally cylindrical wall defining the open end of said case; and
   means for communicating a rehydrating substance from an external source to within the closed case;

(B). separately containing a rehydrating substance;

(C). mixing the dehydrated fetal or cosmetic substance with the rehydrating substance by introducing said rehydrating substance into the closed device; and (D). freezing the rehydrated substance.

9. A kit adapted in use for preparing a freezable substance of fetal or cosmetic origin for cosmetological application, comprising:
   an isothermic case for containing a dehydrated fetal or cosmetic substance;
   a cover for closing and reopening the case, said cover including at least one orifice for communicating a rehydrating substance;
   at least one ampoule for containing a rehydrating substance, said ampoule including a portion adapted in use to be fitted into the orifice of the cover to communicate the rehydrating substance into the closed case to rehydrate the dehydrated fetal or cosmetic substance contained therein; and
   a storage unit having a shape adapted in use for containing the closed case and the ampoule at ambient temperature.

10. A kit according to claim 9, wherein the storage unit includes a bed of expanded foam for protecting the closed case and the ampoule during transportation.

* * * * *